United States Patent [19]

Hasegawa et al.

[11] Patent Number: 4,568,544
[45] Date of Patent: Feb. 4, 1986

[54] AQUEOUS SOLUTION OF A TISSUE PLASMINOGEN ACTIVATOR DISSOLVED THEREIN AT AN INCREASED CONCENTRATION AND A METHOD

[75] Inventors: Akio Hasegawa, Numazu; Shuhei Kondo, Fuji, both of Japan

[73] Assignee: Asahi Kasei Kogyo Kabushiki Kaisha, Osaka, Japan

[21] Appl. No.: 705,896

[22] Filed: Feb. 26, 1985

[30] Foreign Application Priority Data

Feb. 29, 1984 [JP] Japan .................................. 59-35894
Mar. 1, 1984 [JP] Japan .................................. 59-37280

[51] Int. Cl.$^4$ ...................... C12N 9/48; A61K 37/04; A61K 35/48; A61K 37/54
[52] U.S. Cl. .................................. 424/94; 260/112 R; 424/85; 424/95; 424/103; 424/105; 424/113; 435/68; 435/172.3; 435/188; 435/212; 435/215; 435/216; 435/217; 435/240
[58] Field of Search ...................... 424/85, 94, 95, 103, 424/113, 99, 105; 435/188, 68, 172.3, 212, 215, 216, 217, 240; 260/112 R

[56] References Cited

U.S. PATENT DOCUMENTS

| | | | |
|---|---|---|---|
| 3,555,000 | 1/1971 | Wagner et al. | 435/217 X |
| 3,904,480 | 9/1975 | Hull et al. | 435/217 |
| 3,930,945 | 1/1976 | Lewis | 435/215 |
| 3,950,513 | 4/1976 | Jensen | 424/94 |
| 3,998,947 | 12/1976 | D'Hinterland et al. | 424/105 |
| 4,082,612 | 4/1978 | Robbins et al. | 435/216 X |
| 4,083,961 | 4/1978 | D'Hinterland et al. | 424/95 |
| 4,317,882 | 3/1982 | Horiguchi et al. | 435/212 |
| 4,328,314 | 5/1982 | Horiguchi et al. | 435/212 |
| 4,442,213 | 4/1984 | Heber et al. | 435/217 |
| 4,505,893 | 3/1985 | Mori et al. | 435/68 X |

FOREIGN PATENT DOCUMENTS 2119804 11/1983 United Kingdom .

OTHER PUBLICATIONS

Radcliffe et al, Arch. Biochem. Biophys., 189, 185–194 (1978).
Allen, Thromb. Haemostas, 47, 41–45 (1982).

Primary Examiner—Howard E. Schain
Attorney, Agent, or Firm—Birch, Stewart, Kolasch & Birch

[57] ABSTRACT

An aqueous solution of a tissue plasminogen activator dissolved therein at an increased concentration which comprises an aqueous medium and, dissolved therein, a high purity tissue plasminogen activator and at least one dissolution aid selected from the group consisting of lysine, ornithine and salts thereof, and a method for increasing a solubility of a high purity tissue plasminogen activator in an aqueous medium comprising adding said at least one dissolution aid to an aqueous solution of a high purity tissue plasminogen activator. The present aqueous solution contains a high purity tissue plasminogen activator dissolved therein at an increased concentration and the activity of the tissue plasminogen activator can be maintained during handling and storage of the aqueous solution. Therefore, not only can be easily and efficiently performed the treatment of a tissue plasminogen activator in each purification step but also can be stored safely, stably an aqueous tissue plasminogen activator solution as a final product.

20 Claims, No Drawings

AQUEOUS SOLUTION OF A TISSUE PLASMINOGEN ACTIVATOR DISSOLVED THEREIN AT AN INCREASED CONCENTRATION AND A METHOD

This invention relates to an aqueous solution of a tissue plasminogen activator which contains a high purity tissue plasminogen activator at a high concentration. More particularly, the present invention is concerned with an aqueous solution of a tissue plasminogen activator which contains at least one member selected from the group consisting of lysine and ornithine, the tissue plasminogen concentration of which is higher than that of an aqueous solution of the tissue plasminogen activator in which none of lysine and ornithine are contained. The present invention is also concerned with a method for increasing a solubility of a tissue plasminogen activator in an aqueous medium.

As a thrombolytic agent for treating a patient suffering from thrombosis which is caused by the formation of thrombus in a blood vessel, there is known a plasminogen activator. When a plasminogen activator is administered to the patient, the plasminogen activator serves to activate plasminogen in a plasma to form plasmin. The thus formed plasmin serves to digest fibrin which forms the structure of a thrombus, thereby causing thrombolysis. Examples of the conventionally employed plasminogen activator include urokinase obtained from urine or a cultured broth of kidney cells through separation and purification and streptokinase obtained from a cultured broth of Streptococci through separation and purification. However, the use of urokinase and streptokinase has the following disadvantages. Illustratively stated, the affinity of them to fibrin is poor and, therefore, the activation of plasminogen by urokinase and streptokinase to form plasmin occurs almost in a circulating blood but hardly on the thrombus. In that instance, immediately after formation of the plasmin in the circulating blood, the plasmin inevitably undergoes inhibition by a plasmin inhibitor existing in the blood and then is inactivated. For this reason, in order to obtain a satisfactory result in the treatment, it is necessary to administer urokinase or streptokinase in such a large amount that the amount of the formed plasmin in the blood exceeds that of the plasmin inhibitor present in the blood. Further, since the plasmin also digests fibrinogen existing in the blood, if the plasmin is once formed in a large amount in the blood, there is caused such an adverse effect that when the blood vessel is broken, it is no longer possible to repair the broken portion of the blood vessel by means of fibrin to be formed by the activation of fibrinogen and, hence, homorrhage cannot be stopped. Accordingly, if plasmin is able to be formed only on the thrombus constituted mainly of fibrin, the thus formed plasmin scarcely undergoes inhibition by a plasmin inhibitor existing in the circulating blood, and consequently, a satisfactory effect of the treatment can be obtained by a small dose injection without being accompanied by the above-mentioned adverse effect.

Under the situation as mentioned above, a plasminogen activator which has an excellent affinity to fibrin and is effective to thrombolysis by a small dose administration thereof while suppressing side effects to a level as small as possible has been eagerly demanded.

In recent years, as a plasminogen activator of the above-mentioned kind, a tissue plasminogen activator obtained from a culture fluid of human or mammal tissues such as uterus, kidney, lung, small intestine, foreskin and blood vessel wall, a culture fluid of normal cells derived from the above-mentioned tissues, or a culture fluid of tumor cells has been drawn attentions and the use of such a tissue plasminogen activator as a thrombolytic agent is earnestly desired.

Such a tissue plasminogen activator can be obtained from a culture fluid of human or mammal tissues or a culture fluid of cells derived from the tissues through separation and purification. As suitable examples of such a culture fluid, there may be mentioned culture fluids of normal diploid cells derived from human embryonic tissues such as kidney, intestine, lung, thyroid, heart, ureter, skin, foreskin and a whole embryo, human placenta derived cells, or normal diploid cells derived from human tissues such as kidney, intestine, lung, thyroid, heart, ureter and skin. As the culture fluid, there may also be mentioned culture fluids of human melanoma cells [J. Biol. Chem. 256, 7035 (1981)], tumor cells having properties similar to those of the human melanoma cells, and microorganisms or cells which have been prepared by recombinant DNA technique and are capable of producing a tissue plasminogen activator (European patent application Laid-open Specification No. 93619 and British patent application Laid-open Specification No. 2119804). Of them, culture fluids of normal diploid cells of human embryonic kidney, lung or foreskin are more preferable.

The culture fluids may be any of those obtained by cultivating tissues or cells capable of producing a tissue plasminogen activator in various suitable culture media, and examples thereof include such culture fluids as those described in Japanese patent application Laid-open Specification Nos. 107510/1979, 107511/1979, 19001/1980 and 139323/1980, and Japanese Patent Publication Specification No. 5159/1982. Specifically, the culture fluid may be obtained by culturing tissues or cells which are proliferated in a conventional manner for cultivation of animal cells (e.g., as described in *Tissue Culture Methods and Applications*, edited by P. F. Kruse et al, Academic Press, New York, San Francisco, London (1973)) in a nutrient solution containing carbon sources, nitrogen sources and optionally inorganic salts and/or other additives such as amino acids, vitamins, peptides, hormones, saccharides and organic acids. Usually, the culturing is performed using at least 0.2 ml of a nutrient solution per 100,000 cells at a temperature of from 25° to 40 °C., preferably from 35° to 38 °C., thereby to produce a tissue plasminogen activator in the nutrient solution. During the culturing, the pH value of the nutrient solution is adjusted to 6 to 8, preferably 7.0 to 7.4. The culturing period required for the production of a tissue plasminogen activator is usually 4 to 30 days, but may exceed 30 days. Since the rate of production gradually decreases in the later stage of production, the period is chosen so that the best efficiency for commercial production can be attained. Thus, there is obtained a culture fluid which contains the tissue plasminogen activator produced by the tissues or cells.

The overall method for obtaining the tissue plasminogen activator from the above-obtained culture fluid through separation and purification involves steps conventionally employed in protein chemistry, for example, adsorption using carriers, ion exchange, fractional precipitation, gel filtration, electrophoresis, various types of affinity chromatography, especially those using specific antibodies, etc. There can, for example, be used a fibrin Sepharose column chromatography utilizing a fibrin-bonded agarose, a CM Sepharose column chromatography utilizing a carboxymethyl group-bonded agarose, a lysine Sepharose column chromatography utilizing a lysine-bonded agarose, a ligand-exchange chromatography utilizing a zinc chelate agarose, a lectin column chromatography utilizing a concanavalin A-bonded agarose, an affinity chromatography using antibodies specific to the tissue plasminogen activator to be used in the present invention, and a gel filtration method utilizing crosslinked dextran particles. They may be employed either alone or in combination.

A specific one example of the overall method for separating and purifying the tissue plasminogen activator involves adding ammonium sulfate to a culture fluid of the tissue or the cells to form precipitates, separating the thus formed precipitates, dissolving them in an ammonium thiocyanate solution containing sodium chloride, passing the solution through an anti-urokinase Ig-G Sepharose column and applying the solution to a lysine Sepharose column to adsorb the tissue plasminogen activator in the solution onto the column. Thereafter, an eluate obtained by using ε-aminocaproic acid as an eluent is further passed through an anti-urokinase Ig-G Sepharose column, and lyophilized. The thus obtained powder is dissolved in water and is then gel filtered using Sephacryl S-200 (registered trademark by Pharmacia Fine Chemicals AB, Sweden) to obtain the intended plasminogen activator. With respect to the detail of the production of the tissue plasminogen activator, reference may be made to the pending U.S. patent application Ser. No. 519,347 filed Aug. 1, 1983, now U.S. Pat. No. 4,505,893, and European patent application laid-open specification No. 100982.

The tissue plasminogen activator as mentioned above has an excellent affinity to fibrin and an ability to effectively liquefy a thrombus. On the other hand, however, the tissue plasminogen activator has such a disadvantage that the higher the purity of the tissue plasminogen activator, the lower the solubility of the tissue plasminogen activator in an aqueous medium. For example, the tissue plasminogen activator having a purity (the term "purity" will be explained later) of 20,000 units (U)/mg-protein [the term "units (U)" will be explained later] cannot be dissolved in a physiological saline in an amount more than 3,000 U/ml. Therefore, in each purification step in which a large amount of the tissue plasminogen activator is treated, an extremely large volume of a solvent is disadvantageously needed for dissolving the tissue plasminogen activator. Therefore, it has conventionally been difficult to produce a highly purified tissue plasminogen activator effectively and stably on a commercial scale.

The present inventors have made extensive and intensive studies with a view to eliminating the above-mentioned drawbacks. As a result, the present inventors have found that the solubility of a high purity tissue plasminogen activator in an aqueous medium can be remarkably increased by adding to an aqueous solution of a high purity tissue plasminogen activator at least one member selected from the group consisting of lysine, ornithine and salts thereof. The present invention has been made based on such a novel finding.

Therefore, it is an object of the present invention to provide an aqueous solution of a high purity tissue plasminogen activator dissolved therein at an increased concentration.

It is another object of the present invention to provide a method for increasing the solubility of a high purity tissue plasminogen activator in an aqueous solution.

In one aspect of the present invention, there is provided an aqueous solution of a tissue plasminogen activator dissolved therein at an increased concentration comprising:
(1) an aqueous medium;
(2) a tissue plasminogen activator as protein dissolved in said aqueous medium in an amount of 3,000 to 50,000 U/ml based on the aqueous solution; and
(3) at least one member selected from the group consisting of lysine, ornithine and salts thereof dissolved in said aqueous medium at a concentration of 1 mM to a value corresponding to the saturation solubility of said at least one member in said aqueous medium,
said tissue plasminogen activator having a purity of 3,000 to 50,000 U/mg-protein,
the tissue plasminogen activator concentration of said aqueous solution being higher than that of an aqueous solution of the tissue plasminogen activator in which said at least one member is not contained.

In another aspect of the present invention, there is provided a method for increasing a solubility of a tissue plasminogen activator in an aqueous medium, which comprises:
adding to a solution of a tissue plasminogen activator as protein in an aqueous medium at least one member selected from the group consisting of lysine, ornithine and salts thereof in an amount such that the concentration of said at least one member in the resulting aqueous solution becomes 1 mM to a value corresponding to the saturation solubility of said at least one member in said resulting aqueous solution,
said tissue plasminogen activator having a purity of 3,000 to 50,000 U/mg-protein,
thereby enabling the tissue plasminogen activator to dissolve in the aqueous medium at an increased concentration such that the tissue plasminogen activator concentration of said resulting aqueous solution is higher than that of the aqueous solution of the tissue plasminogen activator in which said at least one member is not contained and 3,000 to 50,000 U/ml based on said resulting aqueous solution.

In the present invention, a tissue plasminogen activator is defined as a protein obtained from the above-mentioned culture fluid and having a plasminogen activator activity. Herein, the plasminogen activator activity is also used for expressing the purity of a tissue plasminogen activator and the concentration of an aqueous solution of a tissue plasminogen activator, and is evaluated by the quantity of plasminogen-containing fibrin which is liquefied by the action of a plasminogen activator. The illustrative method for measuring a plasminogen activator activity is as follows.

Using an agar fibrin-added plate prepared using 95 % clotable fibrinogen containing plasminogen (plasminogen content: about 50 casein units/g-clotable protein) as a starting material, the measurement is carried out by a plate method employing urokinase as the standard. A sample solution of a tissue plasminogen activator is diluted with a 0.067 M Tris-HCl buffer (pH 8.0) containing 1 % gelatin, 0.1 M sodium chloride and 0.1 % sodium azide, and the tissue plasminogen activator concentration of the solution exhibiting the lyzing zone of fibrin which is the same as that of 10 International Units (IU)/ml of urokinase on the fibrin plate is designated 10 units/ml ("units" is hereinafter often referred to as "U").

In the present invention, the tissue plasminogen activator has a high purity. The "purity" used herein is expressed in terms of plasminogen activator activity (U) per mg of the tissue plasminogen activator as protein (mg-protein). The purity of the tissue plasminogen activator to be used in the present invention is 3,000 to 50,000 U/mg-protein. The amount of the tissue plasminogen activator as protein may be measured according to the method of Lowry et al. [Lowry, O. H. et al., J. Biol., Chem., 193, 265 (1951)]. The lower limit value of the above-mentioned purity range is a minimum value of the purity of a tissue plasminogen activator which can be recognized as a fraction when subjected to electrophoresis in the purification steps (which will be mentioned later). The upper limit value of the above-mentioned purity range is a value of an about 100 % pure tissue plasminogen activator.

As an aqueous medium used for dissolving the above-mentioned tissue plasminogen activator, there may be employed any of aqueous media which are used for purifying and storing a tissue plasminogen activator. As such an aqueous medium, there may be mentioned, for example, a physiological saline, buffers such as a phosphate buffer, a citrate buffer, an acetate buffer, a tris-HCl buffer and a glycine-NaOH buffer, and the like.

According to the present invention, a tissue plasminogen activator having a purity within the above-mentioned purity range may be dissolved in the above-mentioned aqueous medium in an amount of 3,000 to 50,000 U/ml based on the resulting aqueous solution in the presence of at least one member selected from the group consisting of lysine, ornithine, and salts thereof as a dissolution aid. The tissue plasminogen activator concentration of the resulting aqueous solution is expressed in terms of a value obtained at 0° to 30 ° C. under an atmospheric pressure.

As described before, according to the present invention, there is provided an aqueous solution of a tissue plasminogen activator dissolved therein at an increased concentration. Such provision of a high concentration solution of a tissue plasminogen activator is useful because not only the volume of a solution to be treated in each purification step for obtaining a high purity tissue plasminogen activator from a culture fluid but also the volume of a high purity tissue plasminogen activator solution to be stored can be effectively reduced. For these purposes, the tissue plasminogen activator concentration of the aqueous solution may be preferably 10,000 to 50,000 U/ml, more preferably 30,000 to 50,000 U/ml. In this connection, it should be noted that even with respect to tissue plasminogen activators having a purity within the above-mentioned purity range, i.e. 3,000 to 50,000 U/mg-protein, those having a relatively low purity have a higher solubility in an aqueous medium than that of those having a relatively high purity, and the former without any dissolution aid incorporated therein sometimes exhibits a higher solubility in an aqueous medium than that of the latter with a dissolution aid incorporated therein. Therefore, in the present invention, it is intended to increase a solubility of a tissue plasminogen activator having a certain purity within the above-mentioned purity range in an aqueous medium and provide an aqueous solution of the tissue plasminogen activator at an increased concentration. So, according to the present invention, the tissue plasminogen activator concentration of the aqueous solution is higher than that of an aqueous solution of the tissue plasminogen activator in which said at least one member, namely, dissolution aid is not contained. In order to decrease the volume of the solution in accordance with the purposes as mentioned above, the tissue plasminogen activator concentration of the solution of the present invention may be preferably 2 times or more, more preferably 4 times or more that of an aqueous solution of the tissue plasminogen activator in which the at least one member, namely, dissolution aid is not contained.

In order to attain the above-mentioned concentration range of the tissue plasminogen activator, at least one member selected from the group consisting of lysine, ornithine, and salts thereof as a dissolution aid is dissolved in the aqueous medium at a concentration of 1 mM to a value corresponding to the saturation solubility of the dissolution aid in the aqueous medium. In order to obtain the preferable range of the tissue plasminogen activator concentration as mentioned above, the concentration of the dissolution aid may be preferably 5 to 100 mM, more preferably 10 to 50 mM. When the concentration of the dissolution aid is more than 100 mM, although the above-mentioned preferable range of the tissue plasminogen activator concentration can be attained, the contents of impurities such as metals contained in the dissolution aid tend to be increased and, further, since the dissolution aid renders the solution to be a buffer, it is difficult to change the pH value of the aqueous solution to a desired one. The lysine and ornithine to be used in the present invention may be any of their dextrorotatory isomers, their levorotatory isomers and racemic modification thereof. As the salts of lysine and ornithine, there may be mentioned inorganic acid salts such as hydrochloride, sulfate and nitrate, and organic acid salts such as acetate and propionate. The lysine, ornithine and the salts thereof may be employed either alone or in combination. As the lysine, ornithine and the salts thereof to be used in the present invention, there may be employed those which are commercially available as such. However, if a tissue plasminogen activator solution obtained as a final product is administered by injection, it is preferred to use a dissolution aid of such a grade as will be acceptable for use as an ingredient of a pharmaceutical composition. The concentration of lysine, ornithine and the salts thereof in an aqueous solution may be measured as follows.

To 6 ml of a sample aqueous solution is added 1 ml of 50 w/w % trichloroacetic acid, followed by vigorous stirring for one minute to form precipitates in the resulting reaction mixture. The reaction mixture is subjected to centrifugation at 3000 rpm for 15 minutes to separate into the precipitates and a supernatant. The supernatant is taken out by decantation. The thus obtained supernatant is subjected to evaporation to dryness using a rotary evaporator, thereby to remove trichloroacetic acid from the supernatant. To the resultant is added 10 ml of distilled water, followed by evaporation to dryness using a rotary evaporator. This procedure is repeated three times. Then, the resultant is dissolved in 1.0 ml of 0.02 N aqueous HCl to obtain a sample. The sample is diluted with 0.02 N aqueous HCl so that the concentration of lysine, ornithine and the salts thereof in the resulting solution is in the range of 20 to 500 $\mu$M. 300 $\mu$l of the resulting solution is subjected to determination of the concentrations of lysine, ornithine and the salts thereof in the solution using 835 type high speed amino acid analyzer (manufactured and sold by Hitachi Ltd., Japan). On the other hand, as a standard solution, 300 μl of each 100 μM lysine in 0.02 N aqueous HCl and 100 μM ornithine in 0.02 N aqueous HCl are subjected to determination using the above-mentioned 835 type high speed amino acid analyzer. The data obtained using the sample solution are respectively compared with those obtained using the standard solutions to determine the concentrations of lysine, ornithine and the salts thereof in the sample solution.

The pH value of the aqueous solution of the present invention may generally be 3 to 11. If the pH value of the solution is out of the above-mentioned range, the tissue plasminogen activator may undergo denaturation. Further, the tissue plasminogen activator has an isoelectric point value corresponding to a value of about middle of the above-mentioned pH range and, hence, if the pH value of the aqueous solution of the tissue plasminogen activator is lower than the isoelectric point, the tissue plasminogen activator is caused to have a positive charge. Such a positive charge may kill the effect of the dissolution aid which is a basic amino acid. Therefore, the pH value of the aqueous solution may be preferably 6 to 11.

The tissue plasminogen activator to be used in the present invention is liable to be adsorbed on the wall of a container of the tissue plasminogen activator used in the purification steps and in the storing, and therefore, the handling of the activator may be troublesome. In order to eliminate the above-mentioned drawback, to the aqueous solution of the present invention may be added salts such as sodium chloride and sodium sulfate in an amount such that the concentration of the salt in the resulting aqueous solution becomes 0.02 to 2 M, preferably 0.5 to 2 M.

The aqueous solution of the present invention may be subjected to purification, concentration, lyophylization, etc. and stored at 0° to 30 ° C., preferably 0° to 10 ° C. because if the temperature of the aqueous solution is out of the range of 0° to 30 ° C., the tissue plasminogen activator may be denatured.

According to the present invention, as mentioned above, the above-mentioned dissolution aid is added to an aqueous solution of a tissue plasminogen activator. The addition of the member may be performed at any stage of the production of the tissue plasminogen activator, that is, before and after an aqueous solution of the tissue plasminogen activator is subjected to purification, freezing, thawing, lyophilization, etc. and is stored. In the aqueous solution of the present invention, the solubility and activity of the tissue plasminogen activator can be maintained during the steps of the purification, lyophilization, etc. and during the storage. The aqueous solution of a tissue plasminogen activator of the present invention contains a tissue plasminogen activator having a high purity at an increased concentration as mentioned above. Therefore, according to the present invention, the effective and stable production of a highly purified tissue plasminogen activator on a commercial scale can be ensured. The produced tissue plasminogen activator can be preferably administered intravenously, and the dose, although varying depending on the condition of the patient, may be in the range of 200 –1,000,000 units in terms of plasminogen activator activity per day. The method for intravenous administration is preferably by injection, or it may be administered by dissolving in a transfusion medium etc.

The tissue plasminogen activator can be formulated into, e.g., an injectable preparation, for example, by mixing the substance with a conventional excipient for injection, a buffer (e.g., phosphates, sodium chloride, etc.), an isotonic agent, a filler (e.g., mannitol, dextran, cyclodextrin, etc.), a stabilizer (e.g., gelatin, albumin, sulfites, etc.) or the like, dissolving the mixture in distilled water for injection, and freeze-drying and/or vacuum-drying the solution to obtain a drug composition which is filled in a vial for injection.

Other applications of the plasminogen activator, in addition to medical use as a thrombolytic agent, are for preventing the formation of a thrombus by, for example, combining it with materials such as artificial blood vessels, artificial organs etc., or as a diagnostic agent for thrombosis etc.

The present invention is illustrated in detail with reference to the following Examples, which should not be construed as limiting the scope of the present invention.

EXAMPLE 1

Human embryonic lung cells (manufactured and sold by Flow Laboratories Inc., USA) and Cytodex I (trade mark of bead carrier for cell culture, manufactured and sold by Pharmacia Fine Chemicals AB, Sweden) were implanted in a 12 l spiner flask containing 8 l of Medium MEM (Flow Laboratories Inc., USA) containing 10 v/v % fatal calf serum to obtain a cell suspension having a cell density of $10^5$ cells/ml and a Cytodex concentration of 2.5 mg/ml. The suspension was incubated at 37 ° C. in an air containing 5 v/v % carbon deoxide while stirring at a rotation of 40 rpm. The incubation was performed for 8 days to proliferate the cells so that the cell density of the suspension became $8 \times 10^5$ cells/ml. Then, the culture medium was removed to obtain the bead carrier to which the cells were adhered. The bead carrier was washed with a physiological saline. To the washed bead carrier was added 8 l of serum-free Medium 199 (manufactured and sold by Flow Laboratories Inc., USA) containing 0.5 % by weight of lactalbumin hydrolysate. The resulting mixture was incubated while stirring at a rotation of 60 rpm. The culture medium was replaced on every fifth days, thereby to recover the culture fluid containing a tissue plasminogen activator to be used in the present invention.

32 l of the thus obtained culture fluid was applied to a column ($2.5\phi \times 10$ cm) packed with CM Sepharose (manufactured and sold by Pharmacia Fine Chemicals AB, Sweden) which had been equilibrated with 20 mM acetate buffer (pH 4.0) containing 0.1 v/v % of Tween 80 (manufactured and sold by Wako Pure Chemical Industry Co., Ltd., Japan) and 0.15 M NaCl. The column was washed with the same buffer as mentioned above, and then, elution was conducted using 20 mM tris-HCl buffer (pH 8.9) containing 0.1 v/v % Tween 80 and 1 M NaCl as an eluent to obtain 204 ml of a solution having a plasminogen activator activity. The solution was dialyzed against 20 l of tris-HCl buffer containing 0.1 v/v % Tween 80 and 0.05 M NaCl at 4° C. overnight. The resulting solution was applied to a lysine Sepharose column ($3.6\phi \times 20$ cm) (manufactured and sold by Pharmacia Fine Chemicals AB, Sweden) equilibrated with the same buffer as used in the above-mentioned dialysis and washed with the same buffer. Then, the elution was effected using 20 mM tris-HCl buffer containing 10 mM lysine, 1 M potassium thiocyanate, 0.2 M ε-amino-n-caproic acid and 0.1 v/v % Tween 80 as an eluent to obtain 251 ml of an eluate having a plasminogen activator activity of 3380 U/ml. The eluate was concentrated by ultrafiltration using a SIP type hollow fifer used for ultrafiltration (manufactured and sold by Asahi Kasei Kogyo K.K., Japan) to obtain 30 ml of a solution having a plasminogen activator activity of 27,000 U/ml. The thus obtained solution was subjected to gel filtration using a column (5.0φ×92 cm) packed with Sephacryl S-200 (manufactured and sold by Pharmacia Fine Chemicals AB, Sweden) equilibrated with 20 mM phosphate buffer (pH 7.5) containing 1 M NaCl and 10 mM lysine hidrochloride, thereby to obtain 78 ml of a solution having a plasminogen activator activity. The solution had a tissue plasminogen activator concentration of 9,200 U/ml. The purity of the tissue plasminogen activator thus obtained was 31,000 U/mg-protein.

EXAMPLE 2

The solution obtained in Example 1 was diluted with a physiological saline so that the tissue plasminogen activator concentration of the resulting solution became about 2,000 U/ml. 30 ml of the resulting solution was dialyzed against a buffer containing lysine as indicated in table 1 below at 4° C. overnight. Then, the dialysate was concentrated by ultrafiltration using SIP type hollow fiber (manufactured and sold by Asahi Kasei Kogyo K.K., Japan) so that the volume of the resulting solution became one tenth that of the dialysate. The tissue plasminogen activator concentration of the resulting solution was measured. The results are shown in Table 1. If precipitates were formed in the resulting solution, the tissue plasminogen activator concentration shown in Table 1 was that of the supernatant of the resulting solution.

TABLE 1

| Aqueous medium | | | Before concentration concentration (U/ml) | After concentration | |
|---|---|---|---|---|---|
| L-lysine hydro- (mM) chloride | NaCl (M) | Buffer | | Turbidity | concentration (U/ml) |
| 0 | 0.15 | 20 mM phosphate (pH 7.5) | 1950 | + | 2540 |
| 0 | 1 | 20 mM phosphate (pH 7.5) | 1980 | + | 4050 |
| 1 | 1 | 20 mM phosphate (pH 7.5) | 2010 | + | 4200 |
| 10 | 1 | 20 mM phosphate (pH 7.5) | 2000 | − | 19000 |
| 100 | 1 | 20 mM phosphate (pH 7.5) | 2150 | − | 18500 |
| 10 | 1 | 0.2 M citrate (pH 4) | 2050 | + | 8900 |
| 100 | 1 | 0.2 M citrate (pH 4) | 1990 | + | 14000 |
| 0 | 1 | 20 mM Gly-NaOH (pH 10) | 2040 | + | 5200 |
| 1 | 1 | 20 mM Gly-NaOH (pH 10) | 2100 | + | 8050 |
| 10 | 1 | 20 mM Gly-NaOH (pH 10) | 2060 | − | 20100 | note
*: + precipitates were formed
− no precipitates were formed

EXAMPLE 3

Substantially the same procedures as in Example 1 were repeated to obtain an aqueous solution which contained a tissue plasminogen activator having a purity of 28,000 U/mg-protein, except that human embryonic foreskin cells (Flow Laboratories Inc., USA) were used instead of the human embryonic lung cells. The aqueous solution was diluted with a physiological saline so that the tissue plasminogen activator concentration of the resulting solution became about 2,000 U/ml. 30 ml of the resulting solution was dialyzed against 0.5 M sodium sulfate and lysine as indicated in Table 2 below at 4° C. overnight. The dialysate was concentrated by ultrafiltration using SIP type hollow fiber (manufactured and sold by Asahi Kasei Kogyo K.K., Japan) so that the volume of the resulting solution became one tenth times that of the dialysate. The tissue plasminogen activator concentration of the resulting solution was measured. The results are shown in Table 2.

TABLE 2

| Aqueous solution (20 mM phosphate buffer containing 0.5 M Na2SO4, pH 7.5) | Before concentration concentration (U/ml) | After concentration | |
|---|---|---|---|
| | | Turbidity* | concentration (U/ml) |
| no lysine | 1850 | + | 2030 |
| 1 mM L-lysine hydrochloride | 1920 | + | 3800 |
| 10 mM L-lysine hydrochloride | 1950 | − | 18500 |
| 1 mM D-lysine hydrochloride | 2100 | + | 3200 |
| 10 mM D-lysine hydrochloride | 2020 | − | 18900 |
| 1 mM DL-lysine hydrochloride | 1990 | + | 3650 |
| 10 mM DL-lysine hydrochloride | 1960 | − | 18000 | note
*: + precipitates were formed
− no precipitates were formed

EXAMPLE 4

Substantially the same procedure as in Example 1 were repeated to obtain an aqueous solution of a tissue plasminogen activator dissolved in 20 mM phosphate buffer (pH 7.5) containing 10 mM lysine hidrochloride and 1 M NaCl, except that normal diploid cells (Flow Laboratories Inc., USA) derived from human embryonic kidney were used instead of human embryonic lung cells. The aqueous solution thus obtained was concentrated in substantially the same manner as in Example 2 to obtain an aqueous solution of the tissue plasminogen activator having a tissue plasminogen activator concentration of 20,500 U/ml. 5 ml of the aqueous solution was poured in each of vials. The solutions in vials were frozen at −70° C., and immediately after completion of the freezing, the frozen solution in a vial was thawed and subjected to measurement of the tissue plasminogen activator concentration of the solution. Another vial was stored at −20° C. after completion of the freezing, and was thawed and subjected to measuremmt of the tissue plasminogen activator concentration of the solution. On the other hand, in substantially the same manner as mentioned above, vials containing 5 ml of the aqueous solution of the tissue plasminogen activator were obtained. The vials were subjected to lyophilization at a freezing temperature of −70° C. and a temperature on a shelf of 20° C. for 10 hours. Immediately after completion of lyophilization, the resultant in the vial was dissolved in distilled water so that the volume of the resulting solution became 5 ml. The resulting solution was subjected to measurement of the tissue plasminogen activator concentration. On the other hand, another vial was stored for 30 days at −20° C. after completion of the lyophilization. Then, the resultant in the vial was dissolved in distilled water in the same manner as mentioned above and was subjected to measurement of the tissue plasminogen activator concentration in the resulting solution. The results are shown in Table 3.

TABLE 3

|  | Before freezing | After freezing | | After lyophilization | |
|---|---|---|---|---|---|
|  |  | Immediately after freezing | 30 days after freezing | Immediately after lyophilization | 30 days after lyophilization |
| Appearance | transparent | transparent | transparent | transparent | transparent |
| (U/ml) Concentration | 20500 | 20400 | 20300 | 20650 | 20550 |

EXAMPLE 5

Substantially the same procedure as in Example 1 were repeated to obtain 31 l of the culture fluid. The culture fluid was subjected to column chromatography in substantially the same manner as in Example 1, thereby to obtain 198 ml of a solution having a plasminogen activator activity. The solution was dialyzed and applied to a lysine Sepharose column in substantially the same manner as in Example 1. Then, the elution was effected in substantially the same manner as in Example 1 except that 20 mM tris-HCl buffer containing 10 mM L-ornithine, 1 M potassium thiocyanate and 0.1 v/v % Tween 80 was used as an eluent. Thus, 236 ml of an eluate was obtained. The eluate was concentrated by ultrafiltration in the same manner as in Example 1 to obtain 30 ml of the concentrated solution. The solution was subjected to gel filtration using a column (5.0φ×9.2 cm) packed with Sephacryl S-200 (manufactured and sold by Pharmacia Fine Chemicals AB, Sweden) equilibrated with 20 mM phosphate buffer (pH 7.5) containing 10 mM L-ornithine hydrochloride and 1 M NaCl, thereby to obtain 72 ml of an aqueous solution having a plasminogen activator activity. The aqueous solution had a tissue plasminogen activator activity of 8,800 U/ml. The purity of the tissue plasminogen activator was 29,000 U/mg-protein.

EXAMPLE 6

The solution obtained in Example 5 was diluted with a physiological saline so that the tissue plasminogen activator concentration of the resulting solution became about 2,000 U/ml. 30 ml of the resulting solution was dialyzed against a buffer containing ornithine as indicated in Table 4 below at 4° C. overnight. Then, the dialysate was concentrated by ultrafiltration using SIP type hollow fiber (manufactured and sold by Asahi Kasei Kogyo K.K., Japan) so that the volume of the resulting solution became one tenth that of the dialysate. The tissue plasminogen activator concentration of the resulting solution was measured. The results are shown in Table 4. If precipitates were formed in the resulting solution, the tissue plasminogen activator concentration shown in Table 4 was that of the supernatant of the resulting solution.

TABLE 4

| Aqueous medium | | | Before concentration concentration (U/ml) | After concentration | |
|---|---|---|---|---|---|
| L-ornithine hydrochloride (mM) | NaCl (M) | Buffer |  | Turbidity | Concentration (U/ml) |
| 0 | 0.15 | 20 mM phosphate (pH 7.5) | 2020 | + | 2200 |
| 0 | 1 | 20 mM phosphate (pH 7.5) | 2010 | + | 4300 |
| 1 | 1 | 20 mM phosphate (pH 7.5) | 1950 | + | 4800 |
| 10 | 1 | 20 mM phosphate (pH 7.5) | 1950 | − | 18000 |
| 100 | 1 | 20 mM phosphate (pH 7.5) | 1990 | − | 19500 |
| 10 | 1 | 0.2 M citrate (pH 4) | 2010 | + | 7700 |
| 100 | 1 | 0.2 M citrate (pH 4) | 2070 | + | 9200 |
| 0 | 1 | 20 mM Gly-NaOH (pH 10) | 2030 | + | 4100 |
| 1 | 1 | 20 mM Gly-NaOH (pH 10) | 2100 | + | 6020 |
| 10 | 1 | 20 mM Gly-NaOH (pH 10) | 2060 | − | 18200 | note
*: + precipitates were formed
− no precipitates were formed

EXAMPLE 7

Substantially the same procedures as in Example 5 were repeated to obtain an aqueous solution which contained a tissue plasminogen activator having a purity of 29,000 U/mg-protein, except that human embryonic foreskin cells (Flow Laboratories Inc., USA) were used instead of the human embryonic lung cells. The aqueous solution was diluted with a physiological saline so that the tissue plasminogen activator concentration of the resulting solution became about 2,000 U/ml. 30 ml of the resulting solution was dialyzed against a 20 mM phosphate buffer (pH 7.5) containing 0.5 M sodium sulfate and ornithine as indicated in Table 5 below at 4° C. overnight. The dialysate was concentrated by ultrafiltration using SIP type hollow fiber (manufactured and sold by Asahi Kasei Kogyo K.K., Japan) so that the volume of the resulting solution became on tenth that of the dialysate. The tissue plasminogen activator concentration of the resulting solution was measured. The results are shown in Table 5.

TABLE 5

| Aqueous solution (20 mM phosphate buffer containing 0.5 M Na₂SO₄, pH 7.5) | Before concentration concentration (U/ml) | After concentration | |
|---|---|---|---|
|  |  | Turbidity* | concentration (U/ml) |
| no ornithine | 2100 | + | 2500 |

TABLE 5-continued

| Aqueous solution (20 mM phosphate buffer containing 0.5 M Na$_2$SO$_4$, pH 7.5) | Before concentration concentration (U/ml) | After concentration | |
|---|---|---|---|
| | | Turbidity* | concentration (U/ml) |
| 1 mM L-ornithine hydrochloride | 2050 | + | 3200 |
| 10 mM L-ornithine hydrochloride | 2150 | − | 17200 |
| 1 mM D-ornithine hydrochloride | 2020 | + | 3300 |
| 10 mM D-ornithine hydrochloride | 1980 | − | 17900 |
| 1 mM DL-ornithine hydrochloride | 1920 | + | 3200 |
| 10 mM DL-ornithine hydrochloride | 1950 | − | 18100 | note
*: + precipitates were formed
− no precipitates were formed

EXAMPLE 8

Substantially the same procedure as in Example 5 were repeated to obtain an aqueous solution of a tissue plasminogen activator dissolved in 20 mM phosphate buffer (pH 7.5) containing 10 mM lysine hydrochloride and 1 M NaCl, except that normal diploid cells (Flow Laboratories Inc., USA) derived from human embryonic kidney were used instead of human lung cells. The aqueous solution thus obtained was concentrated in substantially the same manner as in Example 2 to obtain an aqueous solution of the tissue plasminogen activator having a tissue plasminogen activator concentration of 19,800 U/ml. 5 ml of the aqueous solution was poured in each of vials. The solution in vials were frozen at −70° C., and immediately after completion of the freezing, the frozen solution in a vial was thawed and subjected to measurement of the tissue plasminogen activator concentration of the solution. Another vial was stored at −20° C. after completion of the freezing, and was thawed and subjected to measurement of the tissue plasminogen activator concentration of the solution. On the other hand, in substantially the same manner as mentioned above, vials containing 5 ml of the aqueous solution of the tissue plasminogen activator were obtained. The vials were subjected to lyophilization at a freezing temperature of −70° C. and a temperature on a shelf of 20° C. for 10 hours. Immediately after completion of the lyophilization, the resultant in the vial was dissolved in distilled water so that the volume of the resulting solution became 5 ml. The resulting solution was subjected to measurement of the tissue plasminogen activator concentration. On the other hand, another vial was stored for 30 days at −20° C. after completion of the lyophilization. Then, the resultant in the vial was dissolved in distilled water in the same manner as mentioned above and was subjected to measurement of the tissue plasminogen activator concentration in the resulting solution. The results are shown in Table 6.

TABLE 6

| | Before freezing | After freezing | | After lyophilization | |
|---|---|---|---|---|---|
| | | Immediately after freezing | 30 days after freezing | Immediately after lyophilization | 30 days after lyophilization |
| Appearance | transparent | transparent | transparent | transparent | transparent |
| (U/ml) Concentration | 19800 | 20200 | 19900 | 19500 | 19400 |

REFERENTIAL EXAMPLE

Step 1

(Preparation of anti-urokinase IgG antibody Sepharose)

200 ml of Sepharose CL-4B gel (manufactured and sold by Pharmacia Fine Chemicals AB, Sweden) was washed with 1.2 l of distilled water and suspended in 120 ml of distilled water. To the thus obtained suspension was added 10 g of BrCN and allowed to stand for 8 minutes while adjusting the pH value of the suspension at 10.5 to 11.5 with 5 N NaOH. Then, the gels in the suspension were separated by filtration and quickly washed with 1.2 l of a chilled aqueous solution containing 0.1 M NaHCO$_3$, and suspended in 100 ml of an aqueous solution (pH 8) containing 0.1 M NaHCO$_3$ and 0.5 M NaCl. To the suspension was added 16 ml of an aqueous solution of anti-urokinase IgG antibody at a concentration of 25 mg/ml based on the aqueous solution. The resulting mixture was gently stirred at room temperature for 1 hour and at 4° C. overnight, successively. Then, the gels in the mixture were separated, washed with 100 ml of an aqueous solution (pH 8) containing 0.1 M NaHCO$_3$ and 0.5 M NaCl, and suspended in 100 ml of 1 M ethanolamine (pH 8). The suspension thus obtained was stirred at room temperature for 24 hours. Then, the gels in the suspension were separated and washed with 80 ml of an aqueous solution (pH 8) containing 0.1 M NaCl, 90 ml of 0.1 M acetate buffer (pH 4.0) containing 0.5 M NaCl, 80 ml of an aqueous solution (pH 8) containing 0.1 M NaHCO$_3$ and 0.5 M NaCl, 30 ml of 8 M urea and 80 ml of phosphate buffered saline, successively. Thus, the anti-urokinase IgG antibody Sepharose was obtained.

Step 2

(Preparation of fibrin Sepharose)

Substantially the same procedures as in Step 1 above were repeated to obtain a fibrin Sepharose, except that the fibrin was used instead of antiurokinase IgG.

Step 3

(Purification of antigen)

5 l of a culture fluid of human lung cells was obtained in substantially the same manner as in Example 1 except that human lung cells (Flow Laboratories Inc., USA) were used. To the culture fluid was added ammonium sulfate at a concentration of 300 g/l based on the culture fluid. The resulting mixture was allowed to stand at 4° C. overnight to form precipitates. The precipitates were collected by centrifugation and dissolved in a physiological saline containing 0.1 v/v % Tween 80 so that the volume of the resulting solution became 500 ml. The solution contained a tissue plasminogen activator at a concentration of 30 U/ml. The solution was passed through a column (1.6$\phi$×2 cm) packed with the anti-urokinase IgG antibody Sepharose as obtained in Step 1 and was applied to a column (2.6$\phi$×40 cm) packed with the fibrin Sepharose as obtained in Step 2. The column was sufficiently washed with 0.5 M aqueous NaCl containing 0.1 v/v % Tween 80. Then, the elution was effected using 0.5 M aqueous arginine containing 0.1 v/v % Tween 80 as an eluent to obtain 200 ml of an aqueous solution of a tissue plasminogen activator having a tissue plasminogen activator concentration of 71 U/ml. The aqueous solution was dialyzed against a physiological saline containing 0.1 v/v % Tween 80 and applied to concanavalin A Sepharose column (manufactured and sold by Pharmacia Fine Chemicals AB, Sweden) (1.6$\phi$×15 cm). The column was washed with 0.01 M NaCl and 0.1 v/v % Tween 80, followed by elution according to a linearly gradient elution method using the above-mentioned buffer at an initial stage while continuously changing the composition of the buffer to 0.01 M phosphate buffer (pH 7.0) containing 0.4 M $\alpha$-D-methylmannoside, 2 M KSCN and 0.1 v/v % Tween 80, thereby to obtain 35 ml of an aqueous solution having a tissue plasminogen activator concentration of 320 U/ml. The thus obtained solution was concentrated by ultrafiltration and subjected to gel filtration using Sephadex G-150 column (1.6$\phi$×90 cm) (manufactured and sold by Pharmacia Fine Chemicals AB, Sweden), thereby to obtain 16 ml of an aqueous solution of a tissue plasminogen activator which contains a tissue plasminogen activator of a purity of 4910 U/mg-protein at a concentration of 450 U/ml based on the aqueous solution.

Step 4

(Immunization of mice)

100 $\mu$g of the tissue plasminogen activator as obtained in Step 3 above was emulsified in the Freund's complete adjuvants to obtain an emulsion. The emulsion was intradermally administered to BALB/c female mice three times at intervals of 2 weeks. Then, 100 $\mu$g of the tissue plasminogen activator was intraperitoneally administered to the mice to complete the immunization.

Step 5

(Cell fusion)

3 days after completion of the immunization, the mice were sacrificed and the spleens were obtained. The spleen cells were cut into pieces and subjected to filtration using a stainless steel mesh to obtain spleen cells. The cells were suspended in Eagle's minimum essential medium (MEM) to obtain a spleen cell suspension. The spleen cells were washed with the MEM containing a serum three times. On the other hand, mouse myeloma cells P3-x63.Ag8.Ul (hereinafter referred to as "P3U1") (manufactured by Flow Laboratories Inc., USA) were washed with the MEM containing a serum three times. The spleen cell suspension and P3U1 suspension were mixed at a cell number ratio of 10:1 and subjected to centrifugation at 800 rpm for 5 minutes to obtain precipitates. The precipitates were gently loosened and to the resulting precipitates in the centrifuge tube was gradually added 1 ml of MEM containing 44% by weight of polyethylene glycol 2000, followed by slowly rotating the centrifuge tube in a bath at 37° C. for 1 minute, thereby to effect cell fusion. Then, 1 ml of MEM was added to the suspension in the tube and then, 2 ml of MEM was added to the suspension every 1 minute while rotating slowly so that the total volume of the suspension became 10 ml. Then, the suspension was subjected to centrifugation at 600 rpm for 5 minutes to separate into a supernatant and cell precipitates. The supernatant was removed. The cell precipitates were suspended in Rosewell Park Memorial Institute (RPMI) 1640 medium containing 10 v/v % fetal calf serum at a cell concentration of 5×10$^5$ cells/ml. 0.1 ml of the resulting suspension was transplanted in each well of a 96 well microplate (Limbro Co., Ltd., USA). One day later, 0.1 ml of RPMI 1640 medium containing 10 v/v % fetal calf serum and HAT (hypoxanthine 1×10$^{-4}$M, aminopterin 4×10$^{-7}$ M and thymidine 1.6×10$^{-5}$ M) (hereinafter referred to as "HAT medium") was added to each well of the plate. Thereafter, a half volume of the medium in each well was replaced with a fresh HAT medium every third or fourth days. 7 days later, the growth of hybrid cells (hybridoma) was observed in several wells, and 10 to 14 days later, the growth of hybridoma was observed in almost all wells.

Step 6

(Selection and cloning of antibody-producing cells)

50 $\mu$l of the supernatant of each well in which hybridoma was grown was taken out and added to the tissue plasminogen activator solution as obtained in Example 1 which was fixed in each well of a 96 well microplate according to EIA method. 2 wells showed antibody activity. The cells in each of those wells were implanted in each well of a 96 well microplate at a cell concentration of 1 cell/well and cloned, thereby to obtain 2 clones. The clones were multiplied in RPMI 1640 medium containing 10 v/v % fetal calf serum. Then, the multiplied cells were collected and suspended in RPMI 1640 medium containing 10 v/v % fetal calf serum and 10 v/v % dimethylsulfoxide. The resulting suspension was stored in a liquid nitrogen.

Step 7

(Intraperitoneal administration of hybridoma to mice)

1×10$^7$ cells of the hybridoma cells of one clone obtained in Step 6 were intraperitoneally administered to BALB/c mice to which 0.2 ml of 2,6,10,14-tetramethyl pentadecane had been intraperitoneally administered. 10 days after the administration of the cells, 3 to 5 ml/mouse of ascite was collected.

Step 8

(Purification of monoclonal antibody)

10 ml of the ascite obtained in Step 7 was subjected to purification according to the method of Hudson et al. [Practical Immunology, Blackwell Sci. Pub. (1976)] to obtain a purified monoclonal antibody which is capable of bonding to a tissue plasminogen activator.

To 10 ml of the ascites was added 2.66 g of ammonium sulfate (35% saturation) and the resulting mixture was allowed to stand at 4° C. overnight to form precipitates. The mixture was then subjected to centrifugation to obtain the precipitates. The precipitates were dissolved in 5.5 ml of 0.01 M phosphate buffer (pH 8) and the resulting solution was dialyzed against the same buffer having a volume 100 times that of the resulting solution overnight. Then, the dialysate was subjected to centrifugation at 1000 rpm for 5 minutes, thereby to obtain 7 ml of a supernatant. The supernatant was applied to DEAE Sepharose column (manufactured and sold by Pharmacia Fine Chemicals AB, Sweden) (20 ml) equilibrated with 0.01 M phosphate buffer (pH 8). The column was washed with 0.01 M phosphate buffer (pH 8) so that the eluate showed the absorbance at 280 nm of less than 0.02. The elution was effected according to a linearly gradient elution method using the above-mentioned buffer at an initial stage while continuously changing the composition of buffer to 0.01 M phosphate buffer (pH 8) containing 0.2 M NaCl, thereby to obtain a fraction containing the monoclonal antibody. The fraction was determined by the criterion of the antibody activity according to the EIA method and by SDS-polyacrylamide gel electrophoresis. Thus, there were obtained 24 ml of an aqueous solution of the monoclonal antibody dissolved therein 41.6 mg of the antibody.

Step 9

(Preparation of anti-tissue plasminogen activator antibody Sepharose column)

Substantially the same procedures as in Step 1 were repeated to obtain anti-tissue plasminogen activator antibody Sepharose column, except that the monoclonal antibody obtained in Step 8 was used instead of anti-urokinase IgG antibody.

EXAMPLE 9

The bead carrier to which the human embryonic lung cells adhered was obtained in the same manner as in Example 1. The carrier was washed with a physiological saline and suspended in 8 l of Medium 199 containing 1 w/v % proteose pepton (manufactured and sold by Difco Laboratories, USA) and 20 kallikrein inhibitor unit (KIU)/ml of aprotinin. The resulting mixture was incubated in the same manner as in Example 1 to obtain 35 l of the culture fluid. The culture fluid was applied to a column (5.0φ×7.5 cm) packed with CM Sepharose (manufactured and sold by Pharmacia Fine Chemicals AB, Sweden) equilibrated with 20 mM acetate buffer (pH 4.0) containing 0.1 v/v % Tween 80, 0.15 NaCl and 25 KIU/ml aprotinin. The column was washed with the same buffer. The elution was effected using 20 mM tris-HCl buffer (pH 8.9) containing 0.1 v/v % Tween 80, 1 M NaCl, 10 mM lysine hydrochloride and 25 KIU/ml of aprotinine as an eluent to obtain 723 ml of an aqueous solution having a plasminogen activator activity. The thus obtained solution was applied to a column (3.6φ×8 cm) packed with the anti-tissue plasminogen activator antibody Sepharose column obtained in Referential Example which was equilibrated with 0.02 M tris-HCl buffer (pH 7.5) containing 0.5 M NaCl and 25 KIU/ml of aprotinin. The column was washed with the same buffer. The elution was effected using 0.2 M glycine-HCl buffer (pH 2.5) containing 10 mM lysine hydrochloride and 25 KIU/ml of aprotinin as an eluent, thereby to obtain 121 ml of an eluate. The eluate was concentrated by ultrafiltration in the same manner as in Example 1 to obtain 25 ml of the resulting solution. The solution was subjected to gel filtration using a column (5.0φ×90 cm) packed with Sephacryl S-200 (manufactured and sold by Pharmacia Fine Chemicals AB, Sweden) equilibrated with 20 mM phosphate buffer (pH 7.5) containing 1 M NaCl and 10 mM lysine hydrochloride, thereby to obtain 69 ml of an aqueous solution having a plasminogen activator activity. The aqueous solution contained the tissue plasminogen activator at a concentration of 11,000 U/ml based on the aqueous solution and of which the tissue plasminogen activator had a purity of 33,000 U/mg-protein.

In Table 7 below, there were shown the volume, tissue plasminogen activator concentration and total activity of tissue plasminogen activator of the solutions and fractions obtained in the purification steps of the tissue plasminogen activator in Example 9 and also the purity of the tissue plasminogen activator dissolved in the above-mentioned solutions and fractions. As is apparent from Table 7, the activity of the tissue plasminogen activator was maintained during the steps of the purification.

TABLE 7

|  | Volume (ml) | Activity (U/ml) | Total activity (U) | Purity (U/mg) |
|---|---|---|---|---|
| culture fluid | 35000 | 26 | 913000 | 4 |
| CM Sepharose column | 723 | 1170 | 846000 | 2300 |
| Anti-tissue plasminogen activator Sepharose column | 121 | 6820 | 825000 | 29500 |
| Concentration | 25 | 32900 | 823000 | 29400 |
| Gel filtration | 69 | 11000 | 759000 | 33000 |

EXAMPLE 10

Substantially the same procedures as in Example 1 were repeated to obtain 670 ml of an elute by a column chromatography using CM Sepharose column. To the thus obtained solution was added plasmin so that the final concentration of the plasmin in the resulting solution became 0.1 casein unit (CU)/ml, followed by incubation at 37° C. for 60 minutes. The resulting solution was cooled to 4° C. and applied to the same column packed with the anti-tissue plasminogen activator antibody Sepharose column as used in Example 9 wnich was equilibrated with 0.02 M tris-HCl buffer (pH 7.5) containing 0.5 M NaCl. The column was washed with the same buffer. The elution was effected using 0.2 M glycine-HCl buffer (pH 2.5) containing 10 mM ornithine hydrochloride to obtain 105 ml of an eluate. The eluate was concentrated by ultrafiltration in the same manner as in Example 1 to obtain 25 ml of the concentrated solution. The solution was subjected to gel filtration using a column (5.0φ×90 cm) packed with Sephacryl S-200 (manufactured and sold by Pharmacia Fine Chemicals AB, Sweden) equilibrated with 20 mM phosphate buffer (pH 7.5) containing 1 M NaCl and 10 mM ornithine hydrochloride, thereby to obtain 70 ml of an aqueous solution having a plasminogen activator activity. The aqueous solution contained the tissue plasminogen activator at a concentration of 8,800 U/ml based on the aqueous solution and of which the tissue plasminogen activator had a purity of 31,500 U/mg-protein.

What is claimed is:

1. An aqueous solution of a tissue plasminogen activator dissolved therein at an increased concentration comprising:
    (1) an aqueous medium;
    (2) a tissue plasminogen activator as protein dissolved in said aqueous medium in an amount of 3,000 to 50,000 U/ml based on the aqueous solution; and
    (3) at least one member selected from the group consisting of lysine, ornithine and salts thereof dissolved in said aqueous medium at a concentration of 1 mM to a value corresponding to the saturation solubility of said at least one member in said aqueous medium, said tissue plasminogen activator having a purity of 3,000 to 50,000 U/mg-protein, the tissue plasminogen activator concentration of said aqueous solution being higher than that of an aqueous solution of the tissue plasminogen activator in which said at least one member is not contained.

2. An aqueous solution according to claim 1, wherein the tissue plasminogen activator concentration is 10,000 to 50,000 U/ml based on the aqueous solution.

3. An aqueous solution according to claim 2, wherein the tissue plasminogen activator concentration is 30,000 to 50,000 U/ml based on the aqueous solution.

4. An aqueous solution according to claim 1, wherein said at least one member is dissolved in the aqueous medium at a concentration of 5 to 100 mM.

5. An aqueous solution according to claim 4, wherein said at least one member is dissolved in the aqueous medium at a concentration of 10 to 50 mM.

6. An aqueous solution according to claim 1, wherein said tissue plasminogen activator is one obtained from the culture fluid of cells derived from a normal human tissue.

7. An aqueous solution according to claim 6, wherein said cells are derived from human embryonic lung.

8. An aqueous solution according to claim 6, wherein said cells are derived from human embryonic foreskin.

9. An aqueous solution according to claim 6, wherein said cells are derived from human embryonic kidney.

10. An aqueous solution according to claim 1, wherein said tissue plasminogen activator is one obtained from the culture fluid of human melanoma cells.

11. An aqueous solution according to claim 1, wherein said tissue plasminogen activator is one obtained from the culture fluid of microorganisms or cells which have been prepared by recombinant DNA technique and are capable of producing a tissue plasminogen activator.

12. A method for increasing a solubility of a tissue plasminogen activator in an aqueous medium, which comprises:

adding to a solution of a tissue plasminogen activator as protein in an aqueous medium at least one member selected from the group consisting of lysine, ornithine and salts thereof in an amount such that the concentration of said at least one member in the resulting aqueous solution becomes 1 mM to a value corresponding to the saturation solubility of said at least one member in said resulting aqueous solution, said tissue plasminogen activator having a purity of 3,000 to 50,000 U/mg-protein, thereby enabling the tissue plasminogen activator to dissolve in the aqueous medium at an increased concentration such that the tissue plasminogen activator concentration of said resulting aqueous solution is higher than that of the aqueous solution of the tissue plasminogen activator in which said at least one member is not contained and 3,000 to 50,000 U/ml based on said resulting aqueous solution.

13. A method according to claim 12, wherein the concentration of said at least one member is 5 to 100 mM.

14. A method according to claim 13, wherein the concentration of said at least one member is 10 to 50 mM.

15. A method according to claim 12, wherein said tissue plasminogen activator is one obtained from the culture fluid of cells derived from a normal human tissue.

16. A method according to claim 15, wherein said cells are derived from human embryonic lung.

17. A method according to claim 15, wherein said cells are derived from human embryonic foreskin.

18. A method according to claim 15, wherein said cells are derived from human embryonic kidney.

19. A method according to claim 12, wherein said tissue plasminogen activator is one obtained from the culture fluid of human melanoma cells.

20. An aqueous solution according to claim 12, wherein said tissue plasminogen activator is one obtained from the culture fluid of microorganisms or cells which have been prepared by recombinant DNA technique and are capable of producing a tissue plasminogen activator.

* * * * *